US009016472B2

(12) United States Patent
Van der Beek et al.

(10) Patent No.: US 9,016,472 B2
(45) Date of Patent: Apr. 28, 2015

(54) TWO-PART HINGED NEEDLE MAGAZINE

(75) Inventors: Willem Van der Beek, Virum (DK); Thomas Nilsson, Bromma (DK); Steffen Lav, Broenshoej (DK); Maria Bjerregaard Andersen, Frederiksburg (DK); Modesto Javier Mora Benito, Farum (DK); Helle Ravn Thomsen, Roedovre (DK)

(73) Assignee: Novo Nordisk A/S, Bagsvaerd (DK)

( * ) Notice: Subject to any disclaimer, the term of this patent is extended or adjusted under 35 U.S.C. 154(b) by 86 days.

(21) Appl. No.: 13/582,547

(22) PCT Filed: Feb. 9, 2011

(86) PCT No.: PCT/EP2011/051858
§ 371 (c)(1),
(2), (4) Date: Jan. 17, 2013

(87) PCT Pub. No.: WO2011/107330
PCT Pub. Date: Sep. 9, 2011

(65) Prior Publication Data
US 2013/0105345 A1    May 2, 2013

Related U.S. Application Data

(60) Provisional application No. 61/312,810, filed on Mar. 11, 2010.

(30) Foreign Application Priority Data

Mar. 5, 2010    (EP) ...................................... 10155604

(51) Int. Cl.
*B65D 83/02*    (2006.01)
*A61M 5/00*    (2006.01)
(Continued)

(52) U.S. Cl.
CPC ............. *A61M 5/002* (2013.01); *A61M 5/3202* (2013.01); *A61M 5/3205* (2013.01); *B65D 83/02* (2013.01); *B65D 85/24* (2013.01)

(58) Field of Classification Search
CPC ............. A61M 5/3202; A61M 5/3205; A61B 19/0262; B65D 85/24
USPC .................. 206/363–367, 380–383; 604/192, 604/239–243, 263
See application file for complete search history.

(56) References Cited

U.S. PATENT DOCUMENTS 3,074,540 A    1/1963    Beich et al.
5,188,612 A *  2/1993    Herrington et al. ........... 604/192
(Continued)

FOREIGN PATENT DOCUMENTS

CN        201108590 Y    9/2008
EP        1536854 A1     6/2005
(Continued)

*Primary Examiner* — Bryon Gehman
(74) *Attorney, Agent, or Firm* — Wesley A. Nicolas; Reza Green; Richard W. Bork (57) ABSTRACT

A needle magazine (10, 110) for storing a plurality of pen needle assemblies in combination with a plurality of pen needle units is disclosed. The magazines each comprise a first part (11, 111) and a second part (12, 112), each holding a number of pen needle assemblies. The first part (11, 111) and the second part (12, 112) are hinged together by a hinge mechanism (13, 113) such that the pen needle magazine (10, 110) can be folded to be easily carried by a user. The needle magazine (10, 110) also comprises an irreversible locking mechanism (30, 31, 130) such that the needle magazine (10, 110) can be used as a waste bin when discarding the used pen needle assemblies.

3 Claims, 5 Drawing Sheets

(51) Int. Cl.
 *B65D 85/24* (2006.01)
 *A61M 5/32* (2006.01)

(56) References Cited

U.S. PATENT DOCUMENTS

| | | | |
|---|---|---|---|
| 5,325,965 A * | 7/1994 | Kelley | 206/366 |
| 5,829,589 A | 11/1998 | Nguyen et al. | |
| 5,873,462 A | 2/1999 | Nguyen et al. | |
| 7,665,605 B2 * | 2/2010 | Erickson et al. | 206/363 |
| 2001/0014792 A1 | 8/2001 | West et al. | |
| 2002/0014430 A1 | 2/2002 | Groth | |
| 2002/0063074 A1 | 5/2002 | Simm et al. | |
| 2003/0015444 A1 | 1/2003 | Molin et al. | |
| 2004/0054336 A1 | 3/2004 | Klint et al. | |
| 2005/0027211 A1 | 2/2005 | Kuhr et al. | |

FOREIGN PATENT DOCUMENTS

| | | |
|---|---|---|
| FR | 2623403 A1 | 5/1989 |
| JP | 6321268 A | 11/1994 |
| JP | 2000271219 A | 10/2000 |
| WO | 92/12743 A1 | 8/1992 |
| WO | 00/54691 A1 | 9/2000 |
| WO | 02/11798 A1 | 2/2002 |
| WO | 2005/049114 A2 | 6/2005 |
| WO | 2007/132237 A1 | 11/2007 |
| WO | 2009016161 A1 | 2/2009 |
| WO | 2009/136193 A1 | 11/2009 |

* cited by examiner

TWO-PART HINGED NEEDLE MAGAZINE

CROSS-REFERENCE TO RELATED APPLICATIONS

This application is a 35 U.S.C. §371 national stage application of International Patent Application PCT/EP2011/051858 (published as WO 2011/107330), filed Feb. 9, 2011, which claimed priority of European Patent Application 10155604.1, filed Mar. 5, 2010; this application further claims priority under 35 U.S.C. §119 of U.S. Provisional Application 61/312,810, filed Mar. 11, 2010.

THE TECHNICAL FIELD OF THE INVENTION

The invention relates to a needle magazine for holding a plurality of needles which can be individually dispensed from the magazine.

DESCRIPTION OF RELATED ART

People suffering from diabetes have to inject themselves with insulin at a daily basis. For this purpose a great number of different pen systems have been developed over the last 30 years. The typical diabetes patient will require injections of insulin several times during the course of a day. In order to facilitate such injections the patient will need a number of injection needles and in order to prevent skin infections it is recommended to use a new sterile needle for each new injection.

Figure 1:
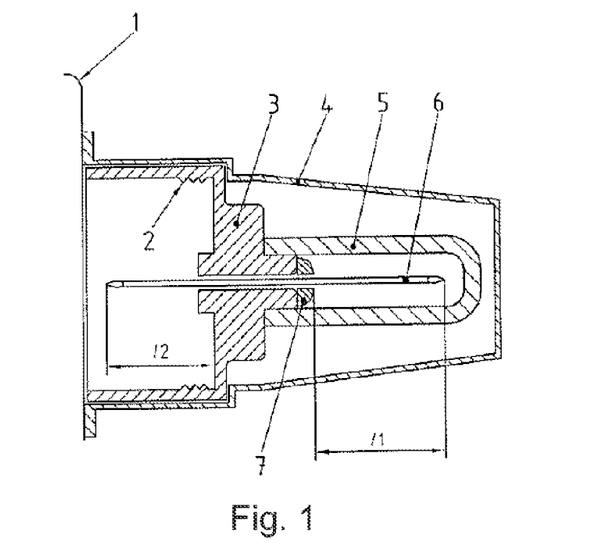
FIG. 1 show a pen needle unit for an insulin pen system.

A prior art pen needle unit for an insulin pen system is disclosed in FIG. 1 and comprises a needle cannula which is mounted in a hub. The needle cannula has an injection part which enters the body during injection and a cartridge part which enters the cartridge contained in the injection pen when the pen needle assembly is connected to the pen system. The pen needle assembly is usually delivered to the user ready-to-use in a sterile container which has an open proximal end sealed by a protective sheet being impermeable to germs and the like. Further the patient end of the needle cannula is often covered by an inner cap as depictured. The hub usually has connecting means located on its inside making it possible to connect the hub to the pen system. Injection needles for pen injectors are further defined in ISO 11608.

Needle units for pen injectors are usually delivered in carton boxes containing 100 pen needle units and a random number of those are carried around by the user loosely in their pockets, purses or briefcases. When carried around loosely there is a great risk that the peel foil protecting the sterility is damaged such that the needle assembly is no longer sterile. Over the years a great number of different magazines for storing and carrying pen needle units have been developed, however many of those are rather large to carry and several have rather complex structure in order to protect the peel foil against damage.

US 2002/0014430, US 2003/0015444 and WO 2005/049114 are examples of such needle magazines for pen needles where a number of pen needle units can be carried in a structured way. These magazines can be refilled with pen needle units by the user and once the pen needle assemblies have been used, the user can remove the used pen needle units and replace them with fresh new ones. In this way, the same needle magazine can be used several times.

A different kind of needle magazine for pen needles is disclosed in WO 02/11798 and in U.S. Pat. No. 5,873,462, here the needle magazine is prefilled by the needle manufacture and once each pen needle assembly have been used the individual pen needle assembly is returned to its compartment in the needle magazine. When all the pen needle assemblies have been used the entire pen needle magazine is discarded. The individual and sterile compartments holding the pen needle assemblies are an integrated part of the magazine and can not be refilled by the user since the compartments are non-sterile once the sealing sheet have been removed and once the used pen needle assembly is returned to its compartment the compartment is contaminated. It is a disadvantage with this type of needle magazine that once discarded access to at least one cartridge part of at least one pen needle assembly is possible thereby exposing a risk since the pen needle assemblies are contaminated once used.

US 2002/0063074 disclose a needle holder for disposal of standard injection needles which is able to hold the non-sterile needle assemblies after use. However, prior to use the user must carry the individual needle assemblies loosely in his or her pocket, purse, briefcase or the like. Once an injection has been performed the user can deliver the used and contaminated needle assembly to the holder.

Needle magazines, which hold a number of injection needles, each contained in its own individual container is e.g. known from WO 92/12743 and from WO 00/54691. In this type of magazine, the needle unit is removed from the magazine before the needle assembly is mounted to the injection device.

A needle magazine with a lid for holding standard injection needles are known from JP 6-321268.

DESCRIPTION OF THE INVENTION

It is an object of the present invention to provide a needle magazine which provides the user with an optimized comfort and safety.

It is especially an object of the present invention to provide a needle magazine that are small in size and easy in use, and which can be carried in the pocket or in the purse of the user without the needle assemblies, especially the peel foil, being damaged and without taken up to much space.

Claim 1

The needle magazine has a first part and a second part that are coupled together through a hinge mechanism thereby making it possible for a user to fold together the needle magazine during transport. Each first and second part holds a number of pen needle assemblies in a number of cavities or compartments provided both in the first and in the second part. The users can then remove one pen needle assembly at the time, perform an injection using an injection device, and return the used pen needle assembly to the pen needle magazine. The pen needle assembly is preferably attached to the injection device by a bayonet coupling as described in EP 1,536,854, and currently provided under the trade name Novotwist®, which only requires a very limited relative rotation between the needle magazine and the injection device in order to secure the needle assembly to the injection device, thereby making it very easy for the user both to remove and to return the used pen needle assembly to and from the needle magazine.

The first and the second parts are preferably, but not necessarily, identical such as disclose in the figures. The two parts are thus provided with the same number of cavities which are preferably located directly opposite each other.

The hinge is provided such that the openings of the compartments abut each other when the needle magazine is folded which makes the transportation of the pen needle magazine very safe since the access to the peel foil is protected by the opposite part. When folded it is not possible for a user to get into contact with the cartridge part of the needle cannula neither before use nor after use. In this way accidental needle stick injuries are prevented.

When unfolding the needle magazine the two parts are swung at an angle relatively to each other such that the first part and the second part move to a position in which they are axially displaced, meaning that the centre axis through the first part and of the second part are no longer the same. Preferably, the opening of each compartment lies in the same plane when the needle magazine is unfolded whereby it becomes very easy for a user to access the compartments using a standard injection pen as currently available. By the same plane is meant that all the openings of all the compartments of both the first and of the second parts are aligned in a parallel planar, i.e. the angle swung is then 180 degrees. However, the needle assemblies can also be removed from the needle magazine with the first part and the second part being in a planar different from parallel e.g. with the two parts being swung at an angle of 90 degrees.

Claim 2-4

Using a double layered sheet material to seal each cavity has the benefit that one of the layers can be folded in a direction away from the pen needle magazine, such that the use can grasp the sheet material from the side of the pen needle magazine pointing away from the hinge mechanism. This secures that the forces used to pull the sheet material is guided away from the hinge mechanism such that the pen needle magazine does not fold during removal of the sheet material. Further, the sheet material can expand outside the boundaries of the pen needle magazine such that the user can inspect if there are unused pen needle assemblies available without having to open the pen needle magazine first.

Claim 5

The needle magazine can in one example be provided with locking means which irreversible locks the two parts together after use. This locking mechanism can be formed as one or more arms or the like provided on one of the two parts which can be moved into engagement with a receiver mechanism provided on the opposite part. The locking mechanism is preferably provided with irreversible locking means, such that when the parts has been locked they can not easily be opened again without the use of tools or without destruction of the locking mechanism. The arm or arms provided on one of the two parts can in a further example be secured to the part through a mechanism that the user must break in order to operate the arm, it could e.g. be an in-moulded tear-line or a spot connection made e.g. by spot welding or by gluing.

Injection needles are usually disposed in special safety sharps containers in which a large numbers of injections needles are collected after use. The safety sharps containers are then delivered back to the pharmacy or the doctor who ships the safety sharps container to a special facility for safe destruction. However, when the needle magazine is provided with an irreversible lock the use of a safety sharp container can be eliminated since the magazine fulfils all the requirements for being a sharps container.

Claim 6

In the disclosed embodiments a resilient bi-stable element can be used. Such bi-stable element has two different positions between which it can shift. When coupled to the needle magazine the two positions would be the folded position or the unfolded position. When a user folds or unfolds the magazine, the bi-stable element will, when its point of no return are reached, assist the user in the folding or unfolding. The resilient bi-stable element is preferably formed as a double S and moulded in one mould with the needle magazine.

Claim 7

The needle magazine could also be provided as a refillable needle magazine in which the compartments holding the pen needle assemblies are in fact the needle container of a pen needle unit. The pen needle unit is preferably secured to the compartment in a non-rotatable way such that the pen needle assembly can be attached to an injection device by rotating the pen needle magazine relatively to the injection device. If a bayonet coupling is used this rotation needs only be a relatively few degrees.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "Needle Cannula" is used to describe the actual conduit performing the penetration of the skin during injection. A needle cannula is usually made from a metallic material and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe a container carrying one single needle assembly as disclosed in FIG. 1. Such container usually has a closed distal end and an open proximal end which is sealed by a removable seal. The interior of such container is usually sterile such that the needle assembly is ready-to-use. Needle units specially designed for pen injections systems are defined in ISO standard No. 11608 and is often referred to as "pen needles".

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

The term "irreversible" is in the context used in this application taken to mean that a number of parts can be permanently locked to each other such that the parts can not be separated again under normal use conditions. "Irreversible locked" would mean that it would not be possible for a user to separate the parts by use of his or her hands. If the parts should be separated it would require the use of some kind of tool such as a knife or a saw and it would render the parts destroyed after separation such that the parts can not perform their normal function again.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 9A-D shows a needle magazine with an alternative partition.

FIG. 10A-C shows a needle magazine with a bi-stable spring element.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" when referring to an injection needle is meant to refer to the end of the needle cannula penetrating the patient whereas the term "proximal end" is meant to refer to the opposite end pointing away from the patient in a situation of use. In the appended figures these terms are used to the needle magazine as with a needle assembly stored in the magazine.

FIG. 1 discloses a prior art pen needle unit as known from ISO 11608. A needle cannula 6 is secured to a hub 3 e.g. by gluing the needle cannula 6 and the hub 3 together using glue 7, however other fastening means could be used. The pen needle assembly (the needle cannula 6 and the hub 3) is delivered to the user in a container 4 which is sealed at the open end with a peel foil 1. The needle cannula has an injection part with a length l1 which enters into the skin of the user during injection and an opposite cartridge part with a length l2 which enters into the cartridge containing the drug to be injected. The injection part is usually covered by an inner cap 5 and the interior part of the container 4 is usually sterilized.

Figure 2:
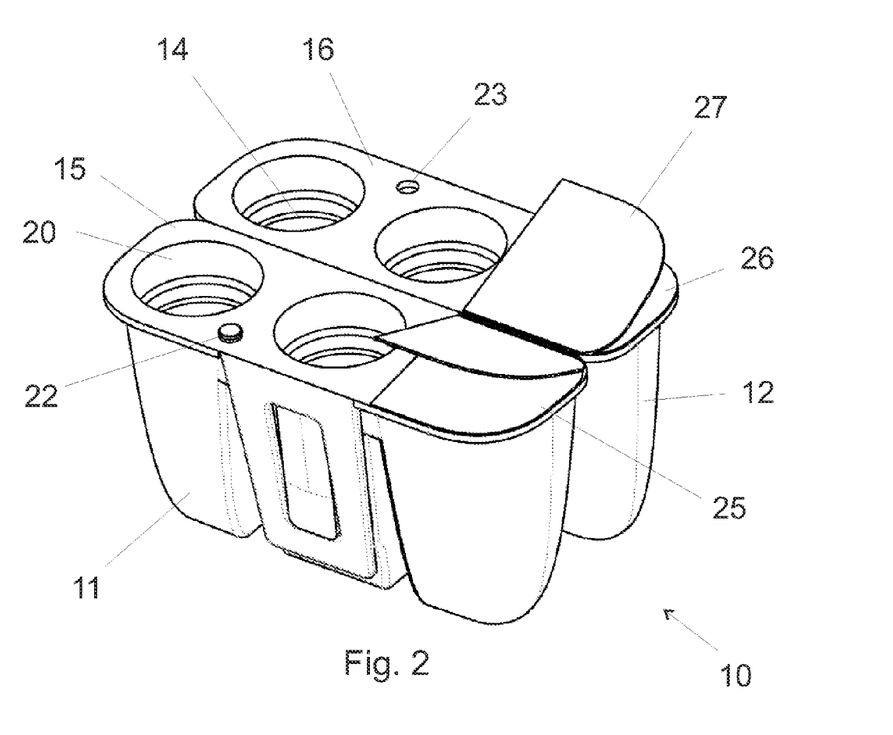
FIG. 2 show a perspective view of a prefilled pen needle magazine.
Figure 3:
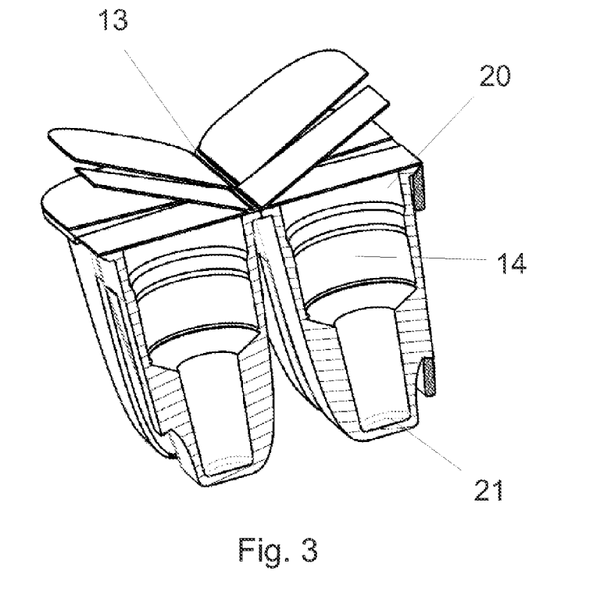
FIG. 3 show a cross sectional view of the prefilled pen needle magazine of FIG. 2.

A prefilled needle magazine 10 is disclosed in FIG. 2 and FIG. 3. The magazine 10 essentially comprises two parts, a first part 11 and a second part 12 which is hinged together by a hinge mechanism 13. The hinge mechanism 13 can be a single film hinge which is moulded in the same operation as the two parts 11, 12 during manufacture as depictured in FIG. 2 and FIG. 3 or it can be any kind of a more complex hinge structure.

The first part 11 has a first top surface 15 and the second part has second top surface 16. The two parts 11, 12 each comprises a number of cavities or compartments 14 which each are configured to hold one single pen needle assembly. The compartments 14 each has a closed distal end 21 and an open proximal end 20 which is sealed by a peel foil 25, the interior is usually sterilized such that the pen needle assembly is kept sterile until the peel foil 25 is removed. In one example the peel foil 25 comprises a first layer 26 and a second layer 27. The first layer 26 is adhered to the magazine 10 and the second layer 27 is folded over the first layer 26. The two layers 26, 27 are connected (preferably by being made from the same sheet) to each other in the proximity of the hinge mechanism 13 such that a user can grasp the second layer 27 of peel foil 25 and pull the peel foil 25 off the magazine 10 in a direction away from the hinge mechanism 13. The second layer 27 can expand beyond the boundaries of the needle magazine 10 such that the user can inspect if there are any unused pen needle assemblies in the needle magazine 10 without opening the folded pen needle magazine 10.

When a user wants to carry the magazine 10 in a purse on in a pocket she can simply fold the two parts 11, 12 of the magazine 10 such that the first top surface 15 abut the second top surface 16 thereby protecting the peel foil 25 from other objects in the purse or in the pocket. The needle magazine 10 is further equipped with a holding mechanism 22, 23 for holding the two parts 11, 12 in the folded position. This holding mechanism 22, 23 can, as depictured in FIG. 2, be a soft tap 22 on the first part 11 which enters a hole 23 in the second part 12 when the magazine 10 is folded, or it can be a more complex connection requiring operation by the user in order to unlock.

Figure 4:
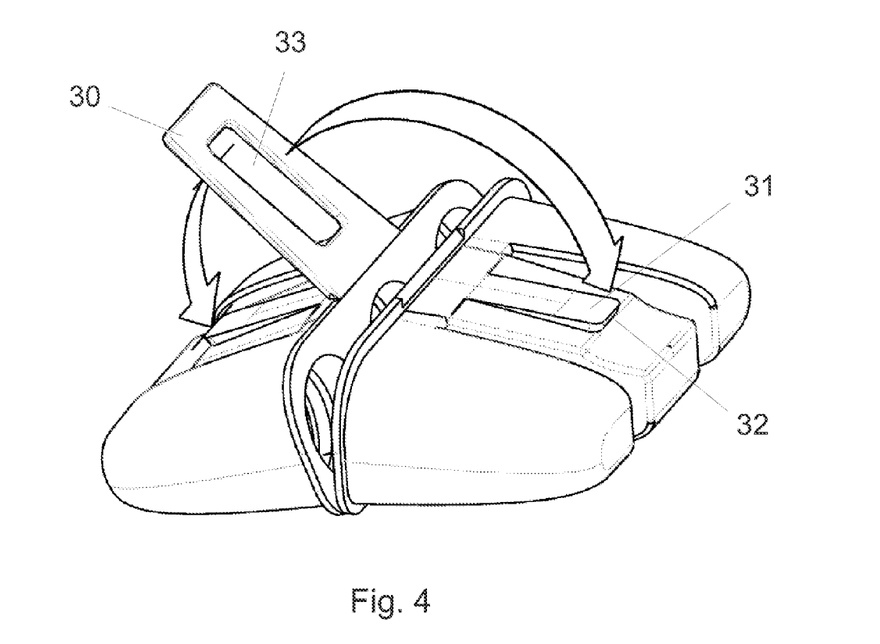
FIG. 4 show a perspective view of the prefilled pen needle magazine in a partly folded position.

The magazine 10 can further be provided with means for permanently locking the two parts 11, 12 to each other in an irreversible way as disclosed in FIG. 4. Once all the pen needle assemblies have been used, the user can move the arm 30 into engagement with the protrusion 31. The protrusion 31 can be provided with an edge 32 over which an opening 33 in the arm 30 can snap in an irreversible way.

Figure 5:
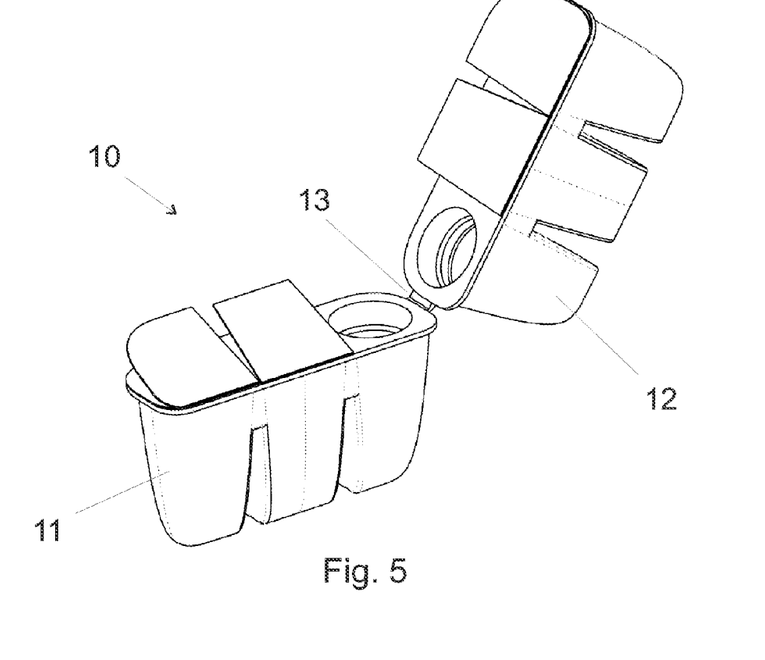
FIG. 5 show a perspective view of an alternative embodiment of a prefilled pen needle magazine.
Figure 6:
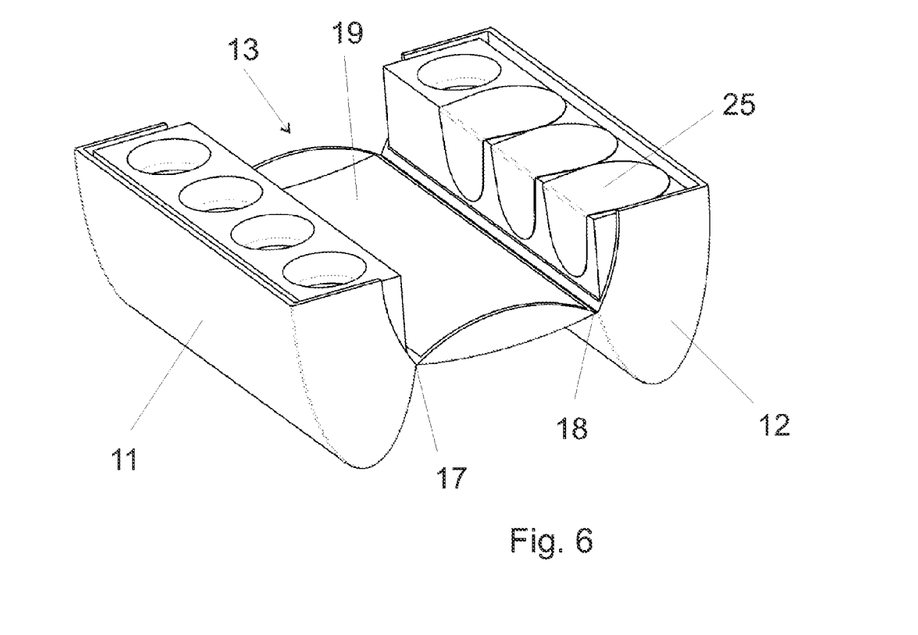
FIG. 6 show a perspective view of another embodiment of a prefilled pen needle magazine.

Further embodiments of the needle magazine are depictured in FIG. 5 and in FIG. 6.

FIG. 5 discloses an embodiment in which the two parts 11, 12 folds out to form an oblong magazine 10 with the hinge mechanism 13 being somewhat narrower than in the previous embodiments.

Figures 9A, 9B, 9C, 9D, 10A, 10B, 10C:
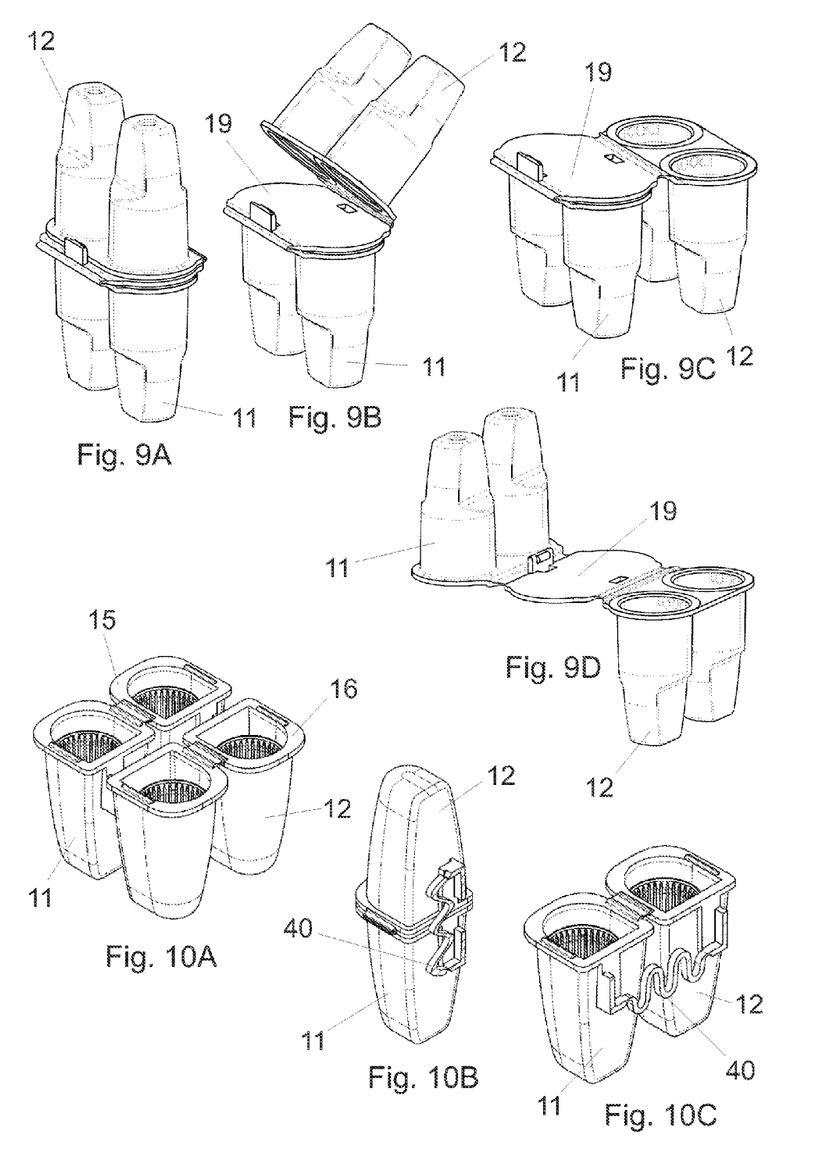

FIG. 6 discloses an embodiment in which the hinge mechanism 13 comprises two film hinges 17, 18 which are separated by a partition 19. In this embodiment the peel foil 25 is formed as a one-layered construction as in the prior art (as depicted in FIG. 1). The partition 19 could also be made from a somewhat soft material such that the whole partition 19 forms the hinge mechanism. An alternative partition 19 is disclosed in the FIGS. 9A to 9D.

Figure 7:
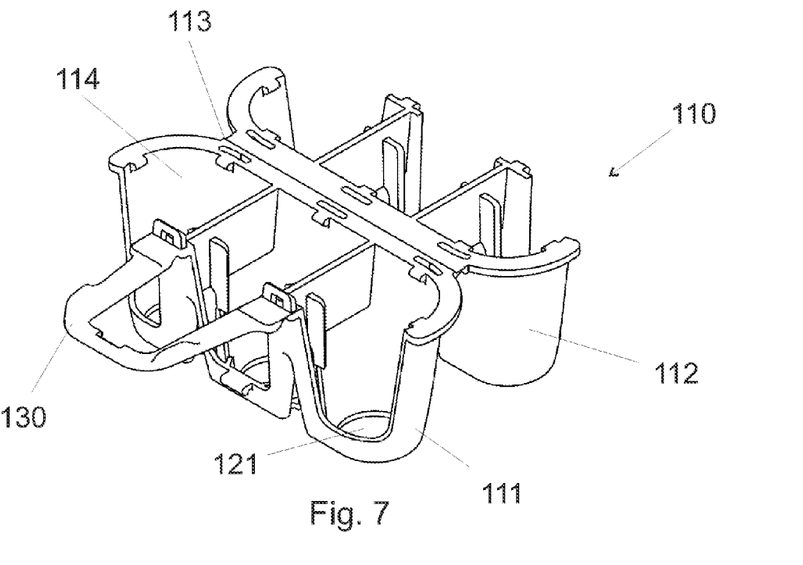
FIG. 7 show an example of a reusable pen needle magazine without needle units.
Figure 8:
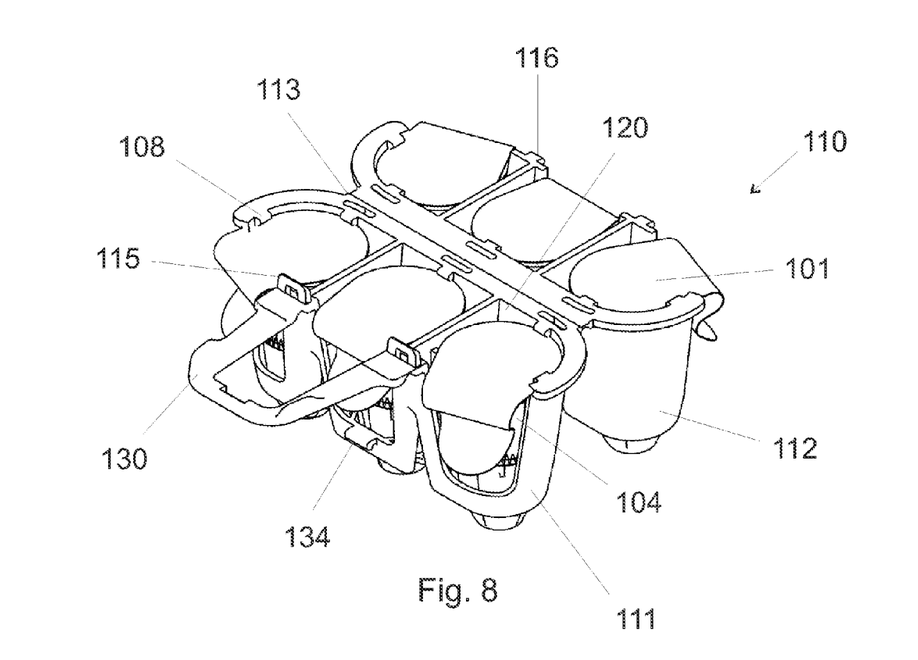
FIG. 8 show an example of a reusable pen needle magazine with needle units.

A refillable needle magazine 110 is disclosed in FIG. 7 and in FIG. 8. The needle magazine 110 essentially comprises two parts 111, 112 that are hinged together by a hinge mechanism 113. Each part 111, 112 has a number of compartments 114 into which compartments 114 the user can load a pen needle unit of the type known from FIG. 1.

Each compartment 114 has at its open proximal end 120 a number of holding means 108 for holding the pen needle unit in place and for allowing the empty pen needle container 104 of the pen needle unit to be replaced when empty. When ready to use as depictured in FIG. 8, each compartment 114 holds a fresh pen needle container 104 each containing one pen needle assembly and each being sealed at the open end by a peel foil 101. At its distal end 121 the pen needle magazine 110 can be formed in a way holding the container 104 of the needle unit inrotatable such that the pen needle assembly can be easily removed without rotating the container inside the pen needle magazine 110. The distal end can e.g. be formed with an opening 121 through which the container 104 can protrude and which opening can be shaped to rotatable secure the container 104.

Further the pen needle magazine 110 comprises an arm 130 which can snap to a not shown receiver mechanism for irreversible locking the needle magazine should the user desire to dispose of the magazine in a safe way. When the arm 130 is not in use it can be secured by a snap lock 134. In this way the reusable needle magazine could be used as a waste bin in the same way as the prefilled pen needle magazines disclosed in FIGS. 2 to 6. For holding the two parts 111, 112 temporarily together during transport a number of taps 115 are provided in one of the two parts 111, 112 and a similar number of receiving protrusions 116 are provided in the opposite part 111, 112.

The first part 11 and the second part 12 is in a further embodiment, disclosed in the FIG. 10A-C, provided with a resilient element 40 which preferably is bi-stable such that it can switch between two different positions only. FIG. 10A discloses such needle magazine with the capacity of holding 4 needle assemblies. In FIG. 10B, the needle magazine 10 is disclosed in its folded position with the first top surface 15 abutting the second top surface 16. The resilient bi-stable element 40 which is attached to the first part 11 and to the second part 12 preferably by moulding is here disclosed in one of its two positions. When the magazine 10 is unfolded the resilient element 40 when reaching a point of no return switches to its second position thereby assisting in the unfolding of the needle magazine 10 into the position disclosed in FIG. 10C. When folded the resilient element 40 works in the opposite direction and assists in folding the needle magazine 10. The bi-stable spring element 40 is in FIG. 10B and FIG. 100 disclosed in a cross sectional view through the needle magazine 10 as disclosed in FIG. 10A, but can easily be implemented for all the embodiments disclosed in the present disclosure.

As depictured in FIG. 9A to 9D the distal end of each compartment can on its outside be formed to enhance the grip. By forming the outside surface with two parallel surfaces at the distal end, the user can grasp each compartment of the needle magazine between his thumb and index finger and twist the magazine. This is a particular advantage if the needle assembly is to be attached to the injection pen via a bayonle coupling which only needs to be twisted (rotated) less than 360 degrees.

Some preferred embodiments have been shown in the foregoing, but it should be stressed that the invention is not limited to these, but may be embodied in other ways within the subject matter defined in the following claims.

The invention claimed is:

1. A needle magazine (10) for storing a plurality of pen needle assemblies and for selectively dispensing the individual pen needle assemblies there from, the needle magazine (10, 110) comprising:
    a first part (11, 111) and a second part (12, 112), wherein the first part (11, 111) and the second part (12, 112) are adapted to store a number of pen needle assemblies in a number of compartments (14, 114) provided in both the first part (11, 111) and in the second part (12, 112), each compartment structured to provide a sterile pen needle assembly in each compartment (14, 114) which is individually sealed by a removable sheet (25, 101), and wherein the first part (11, 111) has a first top surface (15) provided with at least one opening (20) and the second part (12, 112) has a second top surface (16) also provided with at least one opening (20) through which openings (20) the pen needle assemblies can be dispensed, and
    wherein the first part (11, 111) and second part (12, 112) are hinged together by a hinge (13, 113) allowing the first part (11, 111) and the second part (12, 112) to be moved between;
        (i) a folded position in which the first top surface (15) abuts the second top surface (16), such that access to the openings (20, 120) is prevented, and
        (ii) an unfolded position in which each opening (20, 120) can be accessed, and
    wherein the first part (11, 111) and the second part (12, 112) comprises a locking mechanism (30, 31, 130) that irreversibly locks the first part (11, 111) and the second part (12, 112) together in the folded position to prevent access to any of the openings (20, 120) of the compartments (14, 114).

2. A needle magazine according to claim 1, wherein the first part (11, 111) and the second part (12, 112) are provided with a bi-stable resilient element (40) which switches between two different positions only.

3. A needle magazine according claim 1, wherein each compartment (14, 114) is formed by the inside of a plurality of replaceable needle containers (4, 104) secured to the first part (11, 111) and to the second part (12, 112).

* * * * *